United States Patent [19]

Strukel

[11] Patent Number: 5,242,385
[45] Date of Patent: Sep. 7, 1993

[54] ULTRASONIC HANDPIECE

[75] Inventor: Igor Strukel, New York, N.Y.

[73] Assignee: Surgical Design Corporation, Long Island City, N.Y.

[21] Appl. No.: 773,132

[22] Filed: Oct. 8, 1991

[51] Int. Cl.$^5$ .............................................. A61B 17/20
[52] U.S. Cl. ....................... 604/22; 606/169; 128/24 AA
[58] Field of Search ............... 128/24 AA; 604/22; 606/169, 171

[56] References Cited

U.S. PATENT DOCUMENTS

| | | | |
|---|---|---|---|
| 4,169,984 | 10/1979 | Parisi | 310/323 |
| 4,681,561 | 7/1987 | Hood et al. | |
| 4,741,731 | 5/1988 | Starck et al. | 604/22 |
| 4,804,364 | 2/1989 | Dieras et al. | 604/22 |
| 4,808,154 | 2/1989 | Freeman | 604/22 |
| 4,816,017 | 3/1989 | Hood et al. | |
| 4,861,332 | 8/1989 | Parisi | 604/22 |
| 4,978,333 | 12/1990 | Broadwin et al. | 604/22 |
| 4,986,808 | 1/1991 | Broadwin et al. | 604/22 |
| 5,015,227 | 5/1991 | Broadwin et al. | 604/22 |
| 5,038,756 | 8/1991 | Kepley | 604/22 |

FOREIGN PATENT DOCUMENTS 2116045  9/1983  United Kingdom .
WO91/07917  6/1991  World Int. Prop. O. .

Primary Examiner—C. Fred Rosenbaum
Assistant Examiner—Michael Rafa
Attorney, Agent, or Firm—Darby & Darby

[57] ABSTRACT

An ultrasonic transducer of the magnetostrictive type in which the stack of laminations is divided into sections and at least one fluid supply tube extends at least part way along the length of the stack in the space between the two sections. One of the tube supplies irrigation fluid to the interior of the handpiece from which it exits through a sleeve succeeding the transducer tip. An elastic membrane sleeve surrounds the transducer vibrating structure to prevent interaction between the fluid and the transducer and consequent loss of power. The end of the work tip is hollow and the material is drawn therein to be emulsified by the ultrasonic energy radiated from the internal wall of the hollow end.

27 Claims, 2 Drawing Sheets

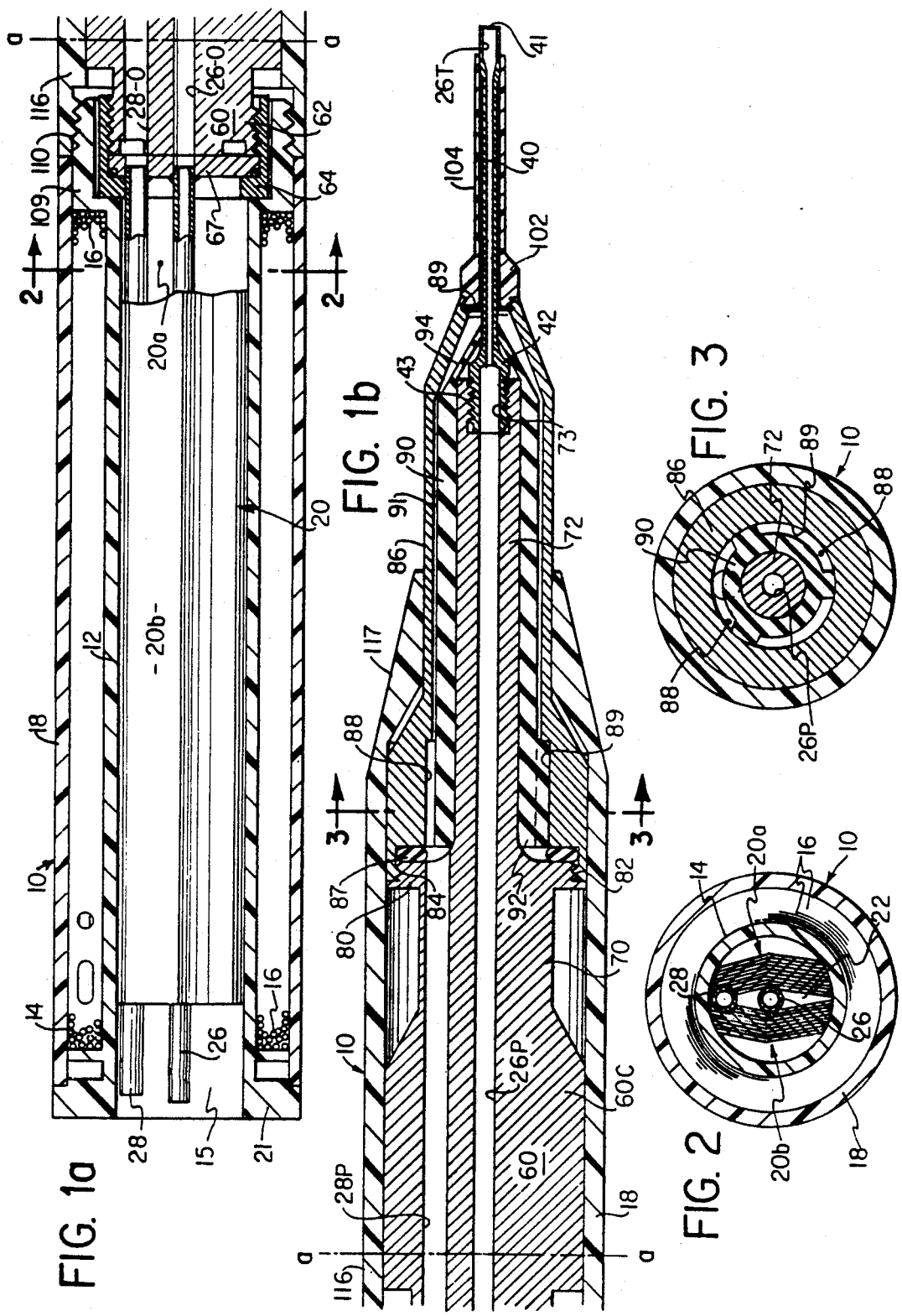

ULTRASONIC HANDPIECE

BACKGROUND OF THE INVENTION

Various types of ultrasonic handpieces are used for surgical application, for example, opthamological surgery for removing cataracts or other tissue. Typically, such handpieces use some type of a vibrating transducer of the magnetostristic or piezoelectric type which converts electrical energy to mechanical vibration.

Such types of ultrasonic handpieces also are capable of supplying irrigation fluid to the operating site in which the transducer is to be used and also to produce a suction pressure for removing the material which has been emulsified by the ultrasonic transducer. It is also known that in such ultrasonic transducers that the irrigation fluid and the suction is supplied through tubes associated with the transducer and are partially or totally within the housing which houses the transducer. Usually in the case of a magnetostristic type of transducer, the tubes are laid along and outside the stack of laminations forming the vibrating structure. It is desirable to reduce the overall size of the housing so that the transducer becomes easier for the user to hold and manipulate.

It is also often desirable to increase the operating power output of such transducers. In magnetostrictive type transducers, this can be done by increasing the size of the lamination stack and/or the coil wire size to provide additional current. Neither approach offers desirable solutions since they increase the transducer size and/or its heat output.

In addition, it is desired to improve the emulsification action and to confine it more closely to or within the work top.

BRIEF DESCRIPTION OF THE INVENTION

The present invention is directed to transducer of the magnetostrictive type which has a reduced size outer housing and also produces additional power without any increase in the size of either the lamination stack or the coil. In accordance with the invention, the lamination stack is split into two parts with interleaved lamination layers. The infusion and suction tubes are totally or partly located within the two parts of the stack. The fluid in the tube or tubes aids in cooling the stack and does not increase the overall size of the handpiece.

In another aspect of the invention, it has been found that the irrigation fluid to be supplied to the operation site interacts with the vibrating structure to produce a cavitation effect which reduces the transducer power output. In accordance with the present invention, an elastic membrane covers the vibrating structure and isolates it from the irrigation fluid. This permits the structure to vibrate more freely with a consequential increase in the transducer power stroke. No increase of either the lamination stack size or coil current is needed.

The invention also includes a novel work tip having an enlarged hollow front end forming a cavity into which the material to be emulsified is drawn. A major part of the ultrasonic energy is radiated within the cavity and the material is emulsified there.

OBJECT OF THE INVENTION

It is therefore an object of the present invention to provide an ultrasonic transducer of the magnetostristic type which has increased power.

An additional object is to provide an ultrasonic transducer in which the lamination stack is cooled by suction liquid or irrigation liquid flowing in a tube which is within the stack.

Still a further object is to provide an ultrasonic transducer in which a membrane is provided between the infusion fluid and the vibrating body which supplies power to vibrate the instrument tip to reduce the formation of air bubbles due to cavitation and thereby to increase the power stroke of the tip.

Another object is to provide an ultrasonic transducer of the magnetostrictive type in which at least a part of one or both of the tubes carrying irrigation and suction fluids are within the lamination stack.

An additional object is to provide an ultrasonic transducer having a work tip where front end has a cavity into which the material is drawn and emulsified by ultrasonic energy produced within the cavity.

BRIEF DESCRIPTION OF DRAWINGS

Other objects and advantages of the present invention will become more apparent upon reference to the following specification and annexed drawings in which:

FIGS. 1a and 1b taken together show a longitudinal view of the ultrasonic handpiece of the subject invention in cross section;

FIG. 2 is a cross-sectional view of a portion of the handpiece looking along lines 2—2 of FIG. 1a;

FIG. 3 is a cross-sectional view of the hand piece taken along lines 3—3 of FIG. 1b;

DETAILED DESCRIPTION OF THE INVENTION

Figure 4:
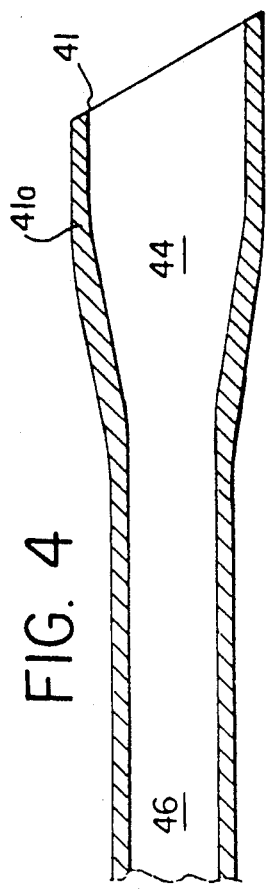
FIG. 4 is an enlarged view of the end of the work tip.

Referring to FIGS. 1a and 1b, where are to be joined together at lines a—a, and FIGS. 2-4, the ultrasonic handpiece 10 includes an elongated generally cylindrical housing 12 of a suitable material, for example, TECHTRON plastic, having an annular recess 14 along its length. Wound around the housing recess 14 along its length is a coil of wire 16. The wire can be either circular in cross section or else, if desired, flattened so that a larger current carrying surface can be provided. The ends of the wire coil (not shown) are connected by any suitable means to a source of voltage of the proper magnitude.

The housing recess 14 with the coil of wire 16 wound thereon is covered by a sleeve 18, also of a suitable plastic material, and there is an end cap 21 which closes the housing structure with the coil 16 thereon.

In the central hollow area 15 of the housing inside of the housing portion 14, a stack of laminations 20 is located. The laminations are elongated and extend for a substantial portion of the length of the housing. The laminations are preferably of nickel, or other suitable material. As shown in FIG. 3, the laminations of the stack 20 are split into two groups 20a and 20b. The individual laminations of each of the stack groups 20a, 20b are bent into a generally L or V-shape and are interleaved with each other while being kept in metallic contact. The two groups of laminations 20a, 20b are then placed adjacent to each other within the housing. As seen on outer set of laminations of each group has the same shape as the inner laminations have progressively larger upper parts.

As seen in FIG. 3, using the split lamination stack 20a, 20b, provides an open central area through which a tube 26 extends for the length. A second tube 28 extends in the open upper top part of the stack along the length of the stack and is only partly enclosed by the ends of the laminations.

Tube 26 is a suction tube, i.e. its end at the end of the handpiece housing 12 adjacent the cap 21 is connected to a suitable suction source (not shown) which serves for the removal of material emulsified by the handpiece. Tube 28 is connected at the end of the housing adjacent the cap 21 to a suitable source of fluid (not shown) and serves as an irrigation channel for fluid to be conveyed to the operating site.

With the arrangement as shown, both of the tubes 26 and 28 are contained substantially within the open central area of the split lamination stack rather than outside of the stack as in prior handpieces. This permits the housing to have a reduced diameter, which is advantageous since it makes the handpiece easier to handle. It also serves to cool the laminations and prevent them from overheating.

The handpiece also has an elongated hollow tip 40 which is vibrated and performs the actual emulsification of the material at the operating site. Tip 40 has an open end 41 which is somewhat enlarged in the shape of a scoop relative to the remainder of the tip length. The end configuration of the tip can be found otherwise, e.g., it can be straight. As explained below, the end configuration 41 has advantages.

The tip 40 is provided with the vibratory energy produced by the lamination stack 20 through a transition body 60, which also is preferably of titanium. The transition body has a first section 62 which is adjacent the end of the lamination stack 20. The transition body first section 62 is coupled to the stack 20 through collar 64 having internal threads which thread onto the end 65 of the transition body against a plate 67, of monel or similar material, to which the ends of the laminations of stack 20 is attached by any suitable arrangement, such as by brazing. By this arrangement, there is a secure mechanical coupling of the end of the lamination stack to the transition body 62 so that the vibratory energy produced by the stack as it is excited by the electrical current is efficiently transmitted to the transition body 60.

The plate 67 has openings 26-0 and 28-0 into which the ends of the tubes 26 and 28 are inserted and are attached thereto in a fluid tight manner, for example, by welding or brazing, if the tubes 26, 28 are of metal, e.g., nickel. If the tubes are of plastic, a suitable adhesive is used.

The transition body 60 continues toward the tip 40 with a central section 60-C, which is its largest diameter portion. The body tapers at 69 to a section of reduced diameter 70 from which extends an elongated cylindrical end section 72 of further reduced diameter to which tip 40 is attached. The free end of the end section 72 has internal threads 73. The connection of the tip 40 to the transition body 60 is accomplished by providing the inner end of the tip with an enlarged neck portion 42 having external threads 43 which mate with threads 73 on the end section 72 of the transition body. In this manner, the vibratory energy produced by the lamination stack 20 is coupled through the transition body 60 to the end 41 of the tip 40.

A passage 26P extends the length of the transducer body to the tip end and a passage 28P to the end of the transition body central section 70.

The reduced diameter section 70 of the transition body has a flange 80 with external threads 82. To this is coupled a metal shell 86, preferably of titanium, which surrounds the elongated end 72 of the transition body and has threads 84 at its end which mate with the threads 82 on the transition body flange 80. An O-ring seal 87 is provided between the shell 86 and the transition body flange 80. The fluid which flows in the aspiration tube and passage 28, 28P leaves the end of passage 28P at a recess 88 and flows within the shell 86 over the outside of an elastic membrane 90, which is described below.

A membrane 90, preferably of silicone plastic, or other suitable elastic plastic material, surrounds the elongated section 72 of the transition body. The membrane 90 has an end 92 of enlarged diameter which fits within a corresponding internal recess 89 of the metal shell 86. As the shell 86 is tightened on the threads 84 of flange 80 the placement of the membrane 90 is secured. The other end 94 of the membrane 90 is tapered and extends over the junction between the transition section 72 and the tip 40 at the threaded members 42, 73.

The proximal end of the shell 86 has internal threads 88 into which the threaded enlarged nose 102 of an elongated tip sleeve 104 is fastened. A tip sleeve 104, of POLYSULFONE or other suitable plastic material, extends for a substantial portion of the length of the tip 40 terminating at its flared end 41. As seen, the center diameter of the sleeve 104 is only slightly larger than the outer diameter of the tip end 41. Thus, there is no large step between the tip and the sleeve which would require a larger mission to the operating site and/or make it more difficult to see the exact placement of the tip at the operating site.

The purpose of the sleeve 104 is to provide a passage and outlet for the irrigation fluid which flows from the end of passage 28P, into the space 87 between the shell and the sleeve 90, between the nose 102 of the tip sleeve 104 and out the end of the tip sleeve at the end 41. This irrigation fluid will exit at the operating site. If desired, the sleeve 104 can have one or more openings on its periphery through which the fluid can escape.

The membrane 90 performs an important function in that it isolates the irrigation fluid from contact with the vibrating transition body end section 72. If there is contact due to the vibration of the transition end section 72, there would be a cavitation effect in the irrigation fluid. This would dissipate power and thereby reduce the amount of power present at the tip end 41. By providing the membrane sleeve 90, the power stroke at the tip end 41 increased, without any change in the other structure of the handpiece, such as the lamination stack 20 on coil 16.

Tube 26 applies suction to the tip 40 to its end 41. This draws the material to be emulsified into the enlarged hollow tip end, which is essentially a cavity. The cavity inner wall radiates the ultrasonic energy within the cavity. The radiation occurs from the internal cavity wall particularly at the internal corners 41a. Thus, the material within the cavity at the tip end is emulsified. The outer rim of the tip end also outwardly radiates some energy but the amount is minor compared to that which is radiated within the cavity. Thus, most of the emulsification occurs within, rather than outside of, the tip.

The emulsified material is conveyed back through the total length of the passage 26-P and the tube 26 and outwardly of the handpiece to a collection chamber (not shown) which is remote from the instrument.

The end of the handpiece housing closest to the tip 40 has a shoulder 109 beyond the point where the housing cover 18 is joined. The shoulder is threaded at 110 and an end housing cover 116, which also can be of the same material as housing 14, is connected thereto. The housing end cover 116 extends for part of the length of the transition member about half way to the part of the reduced diameter section 72. The housing end cover 116 has a tapered end 117 which contacts the shell 86. The person using the hand piece can hold it by the end housing.

Figure 5A:
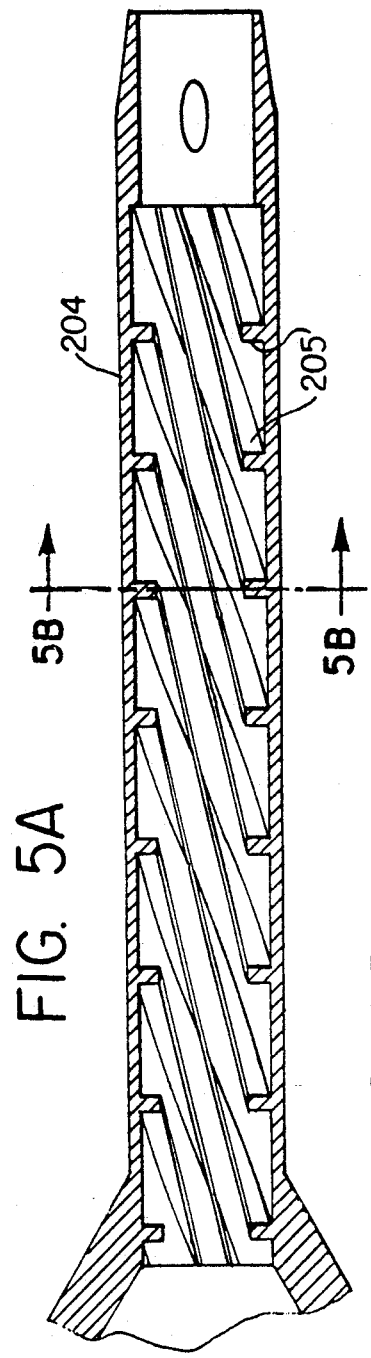
FIGS. 5A and 5B are views of an alternate form of sleeve for the work tip.
Figure 5B:
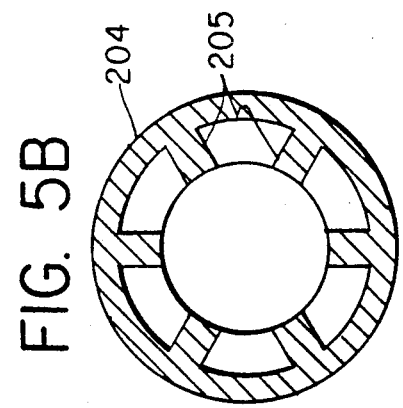

The tip sleeve 104 is illustratively of POLYSUFONE which is a relatively hard plastic. This has an advantage in that it does not absent the ultrasonic energy. In some cases it is preferred that a softer plastic be used. FIGS. 5 and 5A showing another embodiment of the sleeve 204 for securing the tip. Here the sleeve material 204 is of a softer plastic, such as silicone. It has a number of internal helicoidal ribs 205 which run along its length. The ribs 205 engage the outer surface of the tip but leave a space for the fluid to flow. Since the entire inner surface of the sleeve 204 is not in contact with the tip and since the ribs 205 stiffen the sleeve along its length, this reduces the amount of energy that the sleeve absorbs.

As can be seen an improved ultrasonic handpiece has been provided in which the power is increased without increase in size. The handpiece of the present invention can produce the same power as a handpiece of larger size which does not split the lamination stack to accept the fluid tubes and/or which does not use the membrane to prevent cavitation. Further, better control of the emulsification and tissue removal is obtained by the arc of the tip with the cavity.

While the preferred embodiment of the invention has been described with respect to using a magnetostrictive transducer, it should be understood that certain aspects thereof such as the work tip configuration, will also operate with other types of transducers, e.g., piezoelectric.

What is claimed is:
1. An ultrasonic handpiece comprising:
   a housing having a winding therein for receiving electrical voltage
   a plurality of elongated magnetostrictive laminations electrically coupled with said winding to be excited thereby to convert electrical energy into vibrational energy, said plurality of laminations comprising two groups of laminations, the laminations of each group having a generally V-shape and being stacked, the ends of the V-shaped laminations of the two groups facing each other and leaving an open space between the two groups,
   a hollow tip coupled to said laminations to be vibrated thereby, and
   a first fluid supply tube within the open space between the two groups of laminations and extending along at least a portion of the length thereof.
2. An ultrasonic handpiece as in claim 1, further comprising:
   a second fluid supply tube having at least a part thereof between the two groups of laminations and extending for at least a portion of the length thereof; and
   means providing communication between one end of the second tube and the exterior of the handpiece.
3. An ultrasonic handpiece as in claim 2 wherein said first tube is located in the space between the apexes of the facing V-shaped laminations of the two groups and the second tube is located at the ends of the facing laminations of the two groups.
4. An ultrasonic handpiece as in claim 1 further comprising:
   a transition body coupled between the end of the stack and the tip for conveying the stack vibrating energy to said tip, said transition body having a passage extending for a portion of its length for conveying fluid to said tip and a sleeve of elastic material surrounding the exterior surface of the end of the transition body adjacent said tip to prevent fluid from coming into contact with said exterior surface of the transition body.
5. An ultrasonic handpiece as in claim 4 wherein said tip and transition body are coupled by threaded coupling means.
6. An ultrasonic handpiece as in claim 5 wherein said sleeve covers the threaded coupling means.
7. An ultrasonic handpiece as in claim 4 wherein the transition body has first and second sections, the first section coupled to the stack of laminations and the tip being coupled to the second section, the second section being of reduced diameter as compared to the first section.
8. An ultrasonic handpiece as in claim 7 wherein said sleeve covers the second section of said transition body.
9. An ultrasonic transducer as in claim 1 further comprising a shell spaced from and surrounding said transition body second section and said sleeve, the end of said sleeve adjacent said transition body second section having radially outwardly extending means engaging the inner surface of said shell.
10. An ultrasonic handpiece as in claim 1 wherein said tip has a hollow end for receiving therein the material to be emulsified, the interior wall of said hollow end having first and second sections of different diameters which are connected by a transition section defining at least one interior angle between the adjacent ends of the first and second sections, the vibratory energy being transmitted within said hollow end from the part of the interior wall including said at least one angle to act on the material therein.
11. An ultrasonic handpiece comprising:
    means for converting electrical energy into mechanical vibration,
    a work tip coupled to said converting means to receive the mechanical vibration,
    a transition body coupled between the end of the converting means and the tip for conveying the vibration energy to said tip,
    means for supplying fluid to said transition body,
    said transition body having a passage extending for a portion of its length for conveying the fluid to said tip,
    a sleeve of elastic material surrounding the outer surface of the end of the transition body adjacent said tip to prevent fluid from coming into contact with said outer surface of the transition body, and a shell spaced from and surrounding said transition body and said sleeve, the end of said sleeve adjacent said transition body having radially outwardly extending means engaging the inner surface of said shell.

12. An ultrasonic handpiece as in claim 11 wherein said coupling means comprises a vibrating transition body.

13. An ultrasonic handpiece as in claim 12 wherein said work tip and transition body are coupled by threaded coupling means.

14. An ultrasonic handpiece as in claim 13 wherein said sleeve covers the threaded coupling means.

15. An ultrasonic handpiece as in claim 14 wherein the transition body has first and second sections, the first section being coupled to the connecting means and the tip being coupled to the second section.

16. An ultrasonic handpiece as in claim 15 wherein the second section of the transition body is of reduced diameter as compared to the first section.

17. An ultrasonic handpiece as in claim 16 wherein said sleeve covers the second section of said transition body.

18. An ultrasonic handpiece as in claim 12 wherein said fluid supplying means comprises a passage extending for a portion of the length of the transition body, one end of said passage communicating with a source of fluid and the other end of said passage having the fluid exiting therefrom.

19. An ultrasonic handpiece as in claim 18 wherein said connecting means comprises a stack of laminations and means for energizing the stack, and said fluid supplying means further comprises a tube extending along at least part of the length of the stack and having an end communicating with said passage.

20. An ultrasonic handpiece as in claim 19 wherein said tip is hollow, and a second fluid supply tube extending along at least a portion of the length of the stack, one end of said second tube being in communication with the hollow tip.

21. An ultrasonic handpiece as in claim 11 wherein said work tip has a hollow end for receiving therein the material, to be emulsified, the interior wall of said hollow end having first and second sections of different diameters which are connected by a transition section defining at least one interior angle between the adjacent ends of the first and second sections, the vibratory energy being transmitted within said hollow end from the part of the interior wall including said at least one angle to act on the material therein.

22. An ultrasonic handpiece comprising:
means for converting electrical energy into vibratory energy,
a worktip coupled to said converting means to receive the vibratory energy,
said worktip having a hollow end for receiving therein material to be emulsified, the interior wall of said hollow end having first and second sections of different diameters which are connected by a transition section defining at least one interior angle between the adjacent ends of the first and second sections, the vibratory energy being transmitted within said hollow end from the part of the interior wall including said at least one angle to act on the material therein.

23. An ultrasonic handpiece as in claim 2 wherein the exterior of said hollow worktip end is of the same general shape as the interior.

24. An ultrasonic handpiece as in claim 22 further comprising means for applying a suction force to said hollow tip end to draw the material therein.

25. An ultrasonic handpiece as in claim 22 further comprising:
means for converting electrical energy into vibratory energy,
a sleeve surrounding said worktip, said sleeve having an internal wall with flutes thereon to space the sleeve from the worktip.

26. An ultrasonic handpiece as in claim 25 wherein said flutes define a fluid flow passage.

27. An ultrasonic handpiece as in claim 25 wherein said flutes are arranged in a generally spiral pattern.

* * * * *

UNITED STATES PATENT AND TRADEMARK OFFICE
CERTIFICATE OF CORRECTION

PATENT NO.  :  5,242,385
DATED       :  September 7, 1993
INVENTOR(S) :  Igor Strukel It is certified that error appears in the above-indentified patent and that said Letters Patent is hereby corrected as shown below:

Column 8, Claim 23, line 1, "2" should be -- 22 --.

Signed and Sealed this

First Day of August, 1995

Attest:

BRUCE LEHMAN

Attesting Officer

Commissioner of Patents and Trademarks